US011753666B2

(12) United States Patent
Travis

(10) Patent No.: US 11,753,666 B2
(45) Date of Patent: Sep. 12, 2023

(54) METHOD AND SYSTEM FOR PRODUCTION OF ADENOSINE TRIPHOSPHATE

(71) Applicant: Cornell Research Foundation, Inc., Ithaca, NY (US)

(72) Inventor: Alexander Travis, Ithaca, NY (US)

(73) Assignee: CORNELL RESEARCH FOUNDATION, INC., Ithaca, NY (US)

(*) Notice: Subject to any disclaimer, the term of this patent is extended or adjusted under 35 U.S.C. 154(b) by 589 days.

(21) Appl. No.: 16/729,793

(22) Filed: Dec. 30, 2019

(65) Prior Publication Data

US 2020/0131548 A1 Apr. 30, 2020

Related U.S. Application Data

(62) Division of application No. 12/738,367, filed as application No. PCT/US2008/080150 on Oct. 16, 2008, now Pat. No. 10,550,415.

(60) Provisional application No. 60/980,636, filed on Oct. 17, 2007.

(51) Int. Cl.
*C12P 19/32* (2006.01)

(52) U.S. Cl.
CPC .................................. *C12P 19/32* (2013.01)

(58) Field of Classification Search
CPC ........................ C12P 19/32; C12Y 202/01001
See application file for complete search history.

(56) References Cited

U.S. PATENT DOCUMENTS

| | | | |
|---|---|---|---|
| 6,348,348 B1 | 2/2002 | Thompson et al. | |
| 7,332,586 B2 | 2/2008 | Franzen et al. | |
| 2002/0009779 A1 | 1/2002 | Meyers et al. | |
| 2005/0118665 A1 | 6/2005 | Zhou et al. | |
| 2005/0208636 A1 | 9/2005 | Wahlbom et al. | |
| 2005/0281682 A1 | 12/2005 | Paxton et al. | |
| 2008/0199529 A1 | 8/2008 | Franzen et al. | |

OTHER PUBLICATIONS

Hansen et al. Determination of Minute Amounts of ATP by Flow Injection Analysis Using Enzyme Amplification Reactions and Fluorescence Detection; Journal of Biotechnology, vol. 31, pp. 369-380. (Year: 1993).*
Campbell et al. Enzymatic Recycling of Coenzymes by a Multi-Enzyme System Immobilized Within Semipermeable Collodion Microcapsules; Biochmica et Biophysica Acta, vol. 397, pp. 101-109. (Year: 1975).*
Ramachandra et al. Human P-Glycoprotein Exhibits Reduced Affinity for Substrates During a Catalytic Trnsition State; Biochemistry, vol. 37, pp. 5010-5019. (Year: 1998).*
Zhou et al. Lactate Dehydrogenase: Biochemistry and Function of Lactate Dehydrogenase; Cell Biochemistry and Function, vol. 2, pp. 131-134. (Year: 1984).*
Sundaresan et al. Stack of Biocells Converting ATP to Electrical Power and Possible Applications; Materials Research Society Symposium Proceedings, vol. 950, pp. 1-8. (Year: 2007).*
Scheller et al., "Enzyme Electrodes and their Application," Phil. Trans. Soc. London Series B 316, Biological Sciences 85-94 (1987).
Su et al., "Purification of the Type II and Type III Isozymes of Rat Hexokinase, Expressed in Yeast," Protein Expression And Purification 24(1):83-89 (2002).
Du et al., "Motor Protein Nano-Biomachine Powered by Self-Supplying ATP," Chemical Comm. 28(16):2080-2082 (2005).
Kasahara et al., "Reconstituted and Purification of the D-Glucose Transporter from Human Erythrocytes," Journal of Biological Chemistry 252(20):7384-7390 (1977).
Baltazar et al., "Functional Purification of the Monocarboxylate Transporter of the Yeast Candida Utilis," Biotechnol Lett 28(16):1221-1226 (2006).
Slayman, Clifford L., "Plasma Membrane Proton Pumps in Plants and Fungi," Bioscience 35(1):34-37 (1985).
"Tethered To Chip, Energy Supply that Drives Sperm Could Power Nanobot," ScienceDaily http://www.sciencedaily.com/releases/2007/12/071203103420.htm (2007), anonymous.
Nelson, Bryn, "Scientists Look to Sperm to Power Nanobots," Frontiers MSNBC.com http://www.msnbc.msn.com/id/22333518/wid/11915829?gt1=10841 (2008).
Huang et al., "Biological and Biomimetic Molecular Machines", Nanomed 3(1):107-124 (2008).
Choi et al., "Advances in Nano Biotic/Abiotic Hybrid Systems: Protein-Based Engineered Devices", Nanobiotechnology 3:66-75 (2007).
PCT International Search Report and Written Opinion PCT/US2008/080150 dated Oct. 16, 2008.
Eddy et al., "Fibrous Sheath of Mammalian Spermatozoa," Microsc. Res. Technique 61:103-115 (2003).
Storey & Kayne, "Energy Metabolism of Spermatozoa. V. the Embden-Myerhof Pathway of Glycolysis: Activities of Pathway Enzymes in Hypotonically Treated Rabbit Epididymal Spermatozoa," Fertil. Steril. 26(12):1257-1265 (1975).
Travis et al., "A Novel NH2-Terminal, Nonhydrophobic Motif Targets a Male Germ Cell-Specific Hexokinase to the Endoplasmic Reticulum and Plasma Membrane," J. Biol. Chem. 274(48):34467-34475 (1999).
First Office Action for corresponding Chinese Patent Application No. 200880119760.7 (dated Apr. 24, 2012).
Second Office Action for corresponding Chinese Patent Application No. 200880119760.7 (dated Mar. 28, 2013).

(Continued)

*Primary Examiner* — Sharmila G Landau
*Assistant Examiner* — Paul C Martin
(74) *Attorney, Agent, or Firm* — Troutman Pepper Hamilton Sanders LLP (Rochester)

(57) ABSTRACT

The present invention relates to a system for production of ATP. This system is comprised of a support and one or more enzymes coupled to that support which are capable of collectively producing ATP from glucose or fructose metabolism. The present invention is additionally directed to a device, which includes the system, and to a method for carrying out a reaction involving the conversion of ATP to ADP using the system.

21 Claims, 10 Drawing Sheets

Specification includes a Sequence Listing.

(56) References Cited

OTHER PUBLICATIONS

Extended Supplementary Search Report for corresponding European Patent Application No. 08839702.1 (dated Jun. 11, 2012).
Travis et al., "Scaffolded Nanoscale Cellular Energy Production: Can Sperm Help Us Build Nano-machines and Medical Devices?" Poster Presentation, Symposium on Public Engagement and Science Communication, Ithaca, NY (May 14, 2007).
Cao et al., "Proteomic Profiling of Accessory Structures from the Mouse Sperm Flagellum," Mol. Cell. Proteomics 5:801-810 (2006).
Edwards & Grootegoed, "A Sperm-Specific Enolase," J. Reprod. Fert. 68:305-310 (1983).
Feiden et al., "A Novel Pyruvate Kinase (PK-S) from Boar Spermatozoa is Localized at the Fibrous Sheath and the Acrosome," Reproduction 134:81-95 (2007).
Miki et al., "Glyceraldehyde 3-Phosphate Dehydrogenase-S, a Sperm-Specific Glycolytic Enzyme, is Required for Sperm Motility and Male Fertility," Proc. Nat'l. Acad. Sci. U.S.A. 101(47):16501-16506 (2004).
Mori et al., "Mouse Spermatogenic Cell-Specific Type 1 Hexokinase (mHk1-s) Transcripts are Expressed by Alternative Splicing from the mHk1 Gene and the HK1-S Protein Is Localized Mainly in the Sperm Tail," Mol. Reprod. Dev. 49:374-385 (1998).
Mukai & Okuno, "Glycolysis Plays a Major Role for Adenosine Triphosphate Supplementation in Mouse Sperm Flagellar Movement," Biol. Reprod. 71:540-547 (2004).
Travis et al., "Targeting of a Germ Cell-Specific Type 1 Hexokinase Lacking a Porin-Binding Domain to the Mitochondria as Well as to the Head and Fibrous Sheath of Murine Spermatozoa," Mol. Biol. Cell 9:263-276 (1998).
Travis et al., "Functional Relationships Between Capacitation-Dependent Cell Signaling and Compartmentalized Metabolic Pathways in Murine Spermatozoa," J. Biol. Chem. 276(10):7630-7636 (2001).
Travis et al., "Requirements for Glucose Beyond Sperm Capacitation During in Vitro Fertilization in the Mouse," Biol. Reprod. 71:139-145 (2004).
Welch et al., "Expression of a Glyceraldehyde 3-Phosphate Dehydrogenase Gene Specific to Mouse Spermatogenic Cells," Biol. Reprod. 46:869-878 (1992).
Westhoff & Kamp, "Glyceraldehyde 3-Phosphate Dehydrogenase Is Bound to the Fibrous Sheath of Mammalian Spermatozoa," J. Cell Sci. 110:1821-1829 (1997).
Zinkham, "Lactate Dehydrogenase Isozymes of Testis and Sperm: Biological and Biochemical Properties and Genetic Control," Ann. NY Acad Sci. 151(1):598-610 (1968).
Travis & Kopf, "The Spermatozoon as a Machine: Compartmentalized Pathways Bridge Cellular Structure and Function," in Assisted Reproductive Technology: Accomplishments and New Horizons, C.J. De Jonge and C.L. Barratt, eds. (NY:Cambridge University Press) pp. 26-39 (2002).
Chen et al., "Effect of Linker for Immobilization of Glutathione on BSA-Assembled Controlled Pore Glass Beads," Bull. Korean Chem. Soc. 25(9):1366-1370 (2004).
Krisfalusi et al., "Multiple Glycolytic Enzymes are Tightly Bound to the Fibrous Sheath of Mouse Spermatazoa," Biology of Reproduction 75:270-278 (2006).
Skoog et al., "Fructose Determination using Immobilized Enzymes in a Flow System with Special Emphasis on the Effect of Isomerism," Mikrochim Acta III:131-142 (1988).
Caceres et al., "Molecular and Biochemical Characterization of Hexokinase from Trypanosoma Cruzi," Molecular and Biochemical Parasitology 126:251-262 (2003).
Palma et al., "One-Step Purification of a Fully Active Hexahistidine-Tagged Human Hexokinase Type I Overexpressed in *Escherichia coli*," Protein Expression and Purification 22:38-44 (2001).

\* cited by examiner

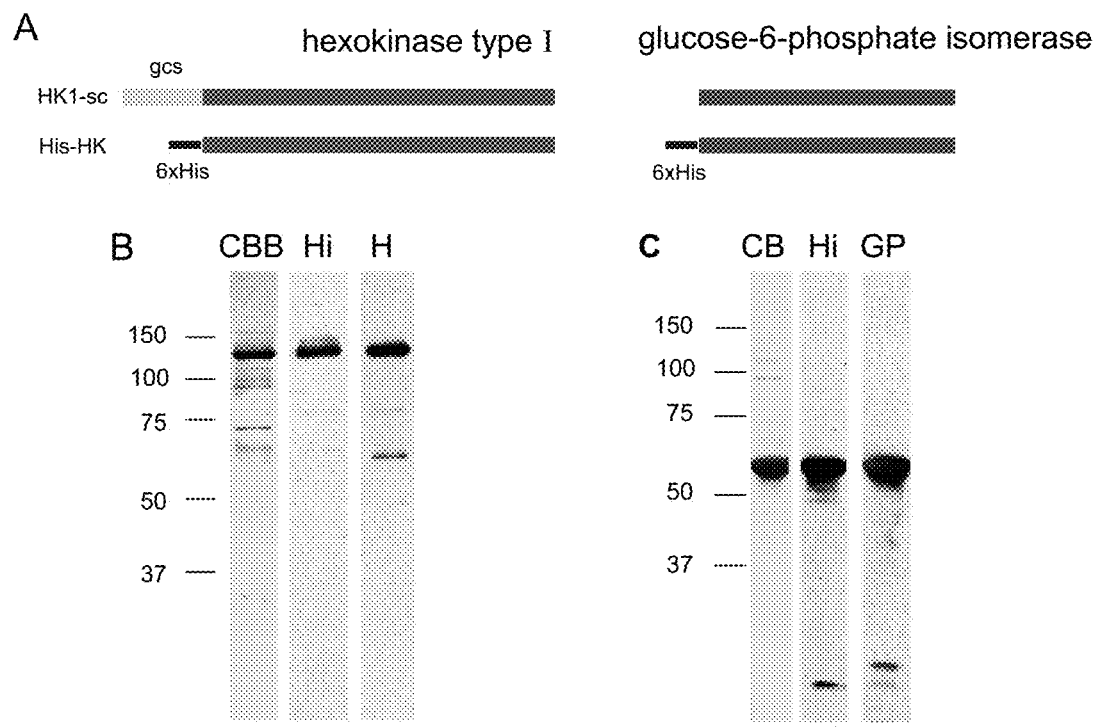
FIGURES 7A-C

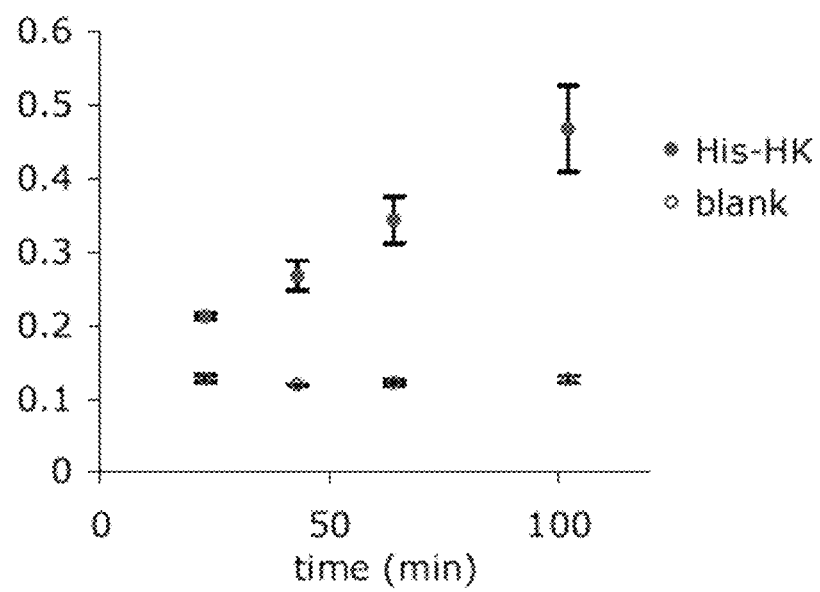
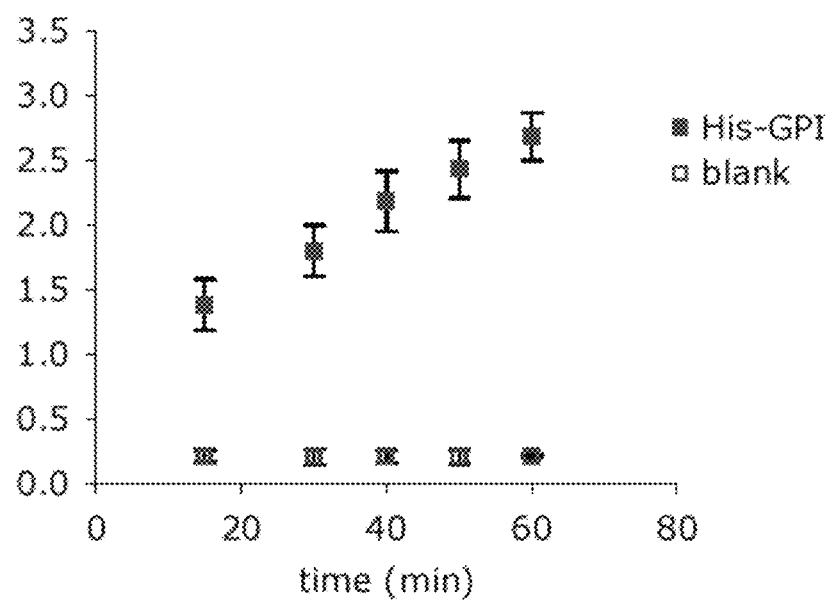
FIGURES 8A-B

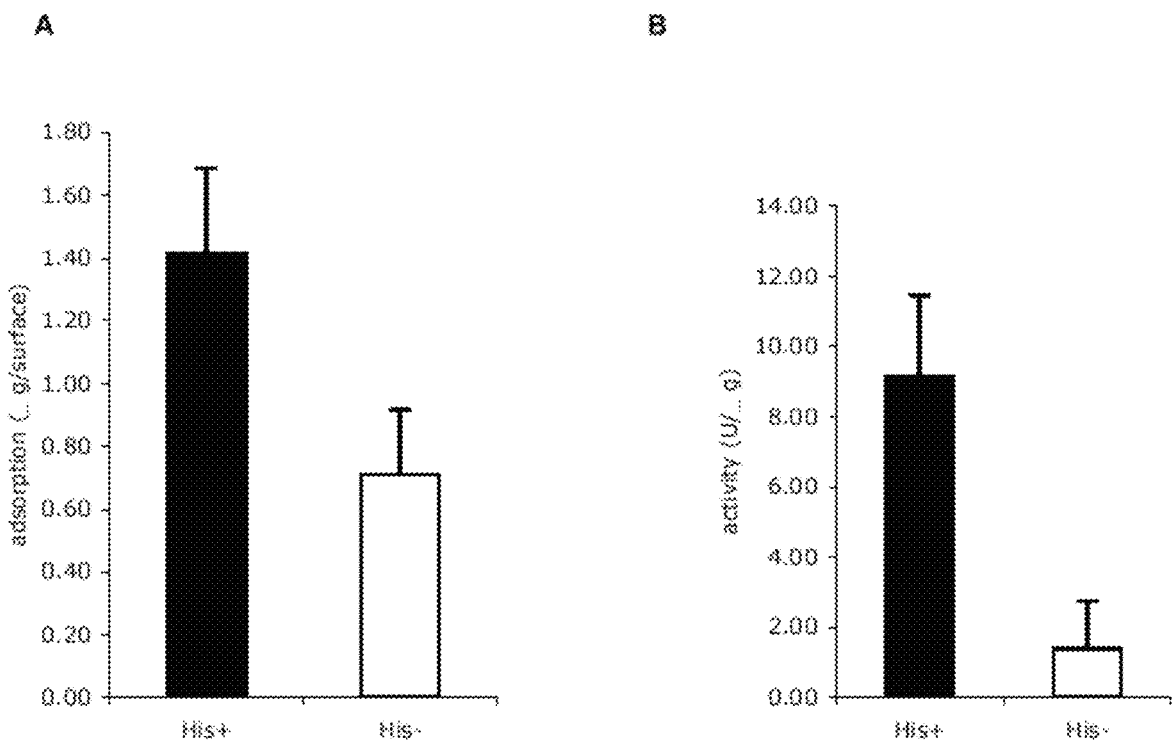
FIGURES 9A-B

METHOD AND SYSTEM FOR PRODUCTION OF ADENOSINE TRIPHOSPHATE

This application is a divisional of U.S. patent application Ser. No. 12/738,367, filed Apr. 16, 2010, and issued as U.S. Pat. No. 10,550,415 on Feb. 4, 2020, which is a national stage application under 35 U.S.C. § 371 of International Patent Application No. PCT/US2008/080150, filed Oct. 16, 2008, which claims the benefit of U.S. Provisional Patent Application Ser. No. 60/980,636, filed Oct. 17, 2007, each of which is hereby incorporated by reference in its entirety.

This invention was made with government support under grant numbers K01-RR00188 and HD-33052 awarded by the National Institutes of Health. The government has certain rights in this invention.

FIELD OF THE INVENTION

The present invention relates to a system for production of adenosine triphosphate ("ATP").

BACKGROUND OF THE INVENTION

One of the most compelling future uses for biotechnology is the generation of hybrid organic-inorganic devices that could carry out biological functions. Applications for such devices are numerous. For example, they could be implanted and perform diagnostic or therapeutic functions, such as supplying needed enzymatic activities or releasing drugs to specific tissues. These devices could circulate within the blood and release a drug or catalyze a reaction upon stimulation by exposure to a specific molecule, pathogen, diseased cell, or tissue type. They might even enter into single cells where they could compensate for a defective or absent biological reaction. Alternatively, they could perform mechanical functions as "nanobots."

Examples of nanoparticle delivery vehicles exist in the art (U.S. Pat. No. 7,332,586 and U.S. Patent Application Publication No. 2008/0199529 to Franzen et al.). However, the applications of a self-powered organic-inorganic device that can carry out biological functions is much more extensive. For example, a hybrid organic-inorganic device which performs biological functions could carry enzymes to replace missing functions, such as a congenital defect where a patient is born without a specific enzyme. This would present an alternative to "gene therapy" in which the patient's DNA has to be altered. Alternatively, one could potentially use such a device to carry an enzyme capable of degrading a toxin or recognizing and destroying a pathogen. Another potential function would be to create a device that could bind to either pathogens or cancer cells, and then specifically pump out a drug or metabolite directly at that cell. Similarly, one could create a device that a surgeon might pack into an infected wound to pump out an antibiotic in an area with poor vascularity. Both approaches would increase the local concentration of that drug and decrease systemic toxicity. However, the problem of how to power such devices—particularly on a very small, nanometer scale—remains a critical obstacle to the development and practical use of such devices.

Examples of hybrid organic-inorganic nanodevices have been reported. For example, a recombinant $F_1$-ATPase has been produced that is tethered to a solid surface on one end and supports a small nickel rod on the other end (Soong et al., "Powering an Inorganic Nanodevice with a Biomolecular Motor," *Science*, 290:1555-8 (2000)). Soong demonstrates that upon hydrolyzing ATP (the most common form of cellular energy for biological reactions), this molecule undergoes a rotary motion and the rod can be seen to move. An "on-off switch" in the form of a reversible binding site has been engineered into this same molecular motor (Liu et al., "Control of a Biomolecular Motor-powered Nanodevice with an Engineered Chemical Switch," *Nat. Mater.*, 1:173-7 (2002)), showing that such devices can be regulated. Similarly, other nanomotors are based on RNA helicases, kinesins, dyneins, or myosin. However, to be functional, ATP must either be provided exogenously or produced locally at the device itself.

A system to generate ATP has been reported, using bacteriorhodopsin and the $F_0F_1$-ATP synthase (Luo et al., "Photo-Induced Proton Gradients and ATP Biosynthesis Produced by Vesicles Encapsulated in a Silica Matrix," *Nat. Mater.*, 4:220-4 (2005); Choi et al., "Advances in Nano Biotic/Abiotic Hybrid Systems: Protein-Based Engineered Devices," *Nanobiotechnol* 3:66-75 (2007)). However, this system requires exogenous light which is not practical for in vivo medical applications.

A second example of a nano-biomachine was created from microtubules and hetero-bifunctional polymer particles bearing pyruvate kinase, which is propelled on glass surfaces coated with kinesin by use of self-supplying ATP (Du et al, "Motor Protein Nano-biomachine Powered by Self-supplying ATP," *Chem Commun.*, 2080-82 (2005)). However, this nano-machine is directed to use in vitro for motility assays with microtubules that travel over glass surfaces. It requires, not glucose or fructose as a starting material, but exogenous adenosine diphosphate ("ADP") and phosphoenol pyruvate ("PEP") to produce ATP.

Attaching or linking proteins to a solid support is well-known in the field. However, maintaining the activity of a protein coupled to a solid support has challenged scientists in the field, and only a few instances of linking a single protein to a solid support and maintaining the activity of that protein have been shown.

The present invention is directed to overcoming these and other deficiencies in the art.

SUMMARY OF THE INVENTION

One aspect of the present invention relates to a system for production of ATP. This system includes a support and one or more enzymes coupled to that support which are capable of collectively producing ATP from glucose or fructose metabolism.

Another aspect of the present invention relates to a device for carrying out a reaction involving the conversion of ATP to ADP. This device comprises a system for producing ATP which includes a support and one or more enzymes coupled to that support which are capable of collectively producing ATP from glucose or fructose metabolism. The device additionally includes components associated with this system and capable of converting ATP to ADP and carrying out the reaction.

The present invention also relates to a method for carrying out a reaction involving the conversion of ATP to ADP. This method involves providing a system for producing ATP from glucose or fructose metabolism. The system includes support and one or more enzymes coupled to the support that are capable of collectively producing ATP from glucose or fructose metabolism. The system is contacted with glucose or fructose under conditions effective to produce ATP from glucose or fructose metabolism. The ATP is converted to ADP, and the reaction is carried out.

A further embodiment of the present invention also relates to a method for producing ATP. This involves providing a system for producing ATP from glucose or fructose metabolism. The device includes a support and one or more enzymes coupled to the support that are capable of collectively producing ATP from glucose or fructose metabolism. The system is contacted with glucose or fructose under conditions effective to produce ATP from the glucose or fructose metabolism.

The present invention involves an improved mechanism to produce ATP for in vivo medical applications. This constitutes a significant advance in sequentially tethering enzymes in a pathway to a solid support and having those enzymes consecutively carry out their functions. This constitutes a new approach for generating ATP from glucose or fructose present in serum in vivo.

BRIEF DESCRIPTION OF THE DRAWINGS

FIGS. 7A-C show the design of recombinant proteins and verification of purified His-HK and His-GPI. In FIG. 7A, hexahistidine tags were introduced to the N-termini of HK and GPI. The known germ cell-specific targeting domain of HK1-sc was directly replaced by the His-tag. SDS-PAGE and immunoblot analysis of His-HK (FIG. 7B) and His-GPI (FIG. 7C) were performed as a quality control of the purification process and to verify the identity of the products. Cooniassie brilliant blue (CBB) staining was performed to visualize the total proteins that were present at the end of purification. An antibody against the His tag (His) indicated the apparent molecular weights of proteins containing the tag, and antibodies against HK (HK) and GPI (GPI) were used to confirm the identity of the enzymes.

FIGS. 8A-B show the activities of bound His-HK and His-GPI when tethered individually. The recombinant proteins were tethered to gold chips with Ni-NTA surfaces and washed well to remove any loosely bound or unbound proteins. Coupled enzymatic reactions were used to determine the activities of the proteins bound to the supports, with a change in absorbance at 340 nm measured spectrophotometrically, as described. Activities represent means from n=9 samples, with 3 samples from each of 3 protein preparations. Bars indicate the standard deviations.

FIGS. 9A-B show that the use of the amino terminal His-tag/Ni-NTA attachment chemistry improved binding and the specific activity of the GPI relative to GPI randomly adsorbed to the surface. The His-tag was cleaved from His-GPI by means of an enterokinase site provided by the expression vector. In FIG. 9A, approximately twice as much His-GPI binds to a Ni-NTA support in comparison with control GPI lacking the His-tag (p=1.012, paired student T test; n=9 samples, with 3 samples from each of 3 protein preparations. Bars indicate the standard deviations). FIG. 9B shows normalizing for the amount of protein bound allowed a quantification of the specific activities of the adsorbed proteins. The specific activity of the His-GPI was approximately 9 times greater than that of the randomly absorbed GPI, although the enzyme activities in solution were relatively equal (p=0.006, paired student T test; n=9 samples, with 3 samples from each of 3 protein preparations. Bars indicate the standard deviations).

DETAILED DESCRIPTION OF THE INVENTION

One aspect of the present invention relates to a system for producing ATP. This system includes a support and one or more enzymes coupled to that support which are capable of collectively producing ATP from glucose or fructose metabolism.

Another aspect of the present invention relates to a device for carrying out a reaction involving the conversion of ATP to adenosine diphosphate ("ADP"). This device comprises a system for producing ATP which includes a support and one or more enzymes coupled to that support which are capable of collectively producing ATP from glucose or fructose metabolism. The device additionally includes components associated with this system and capable of converting ATP to ADP and carrying out the reaction.

Figure 1:
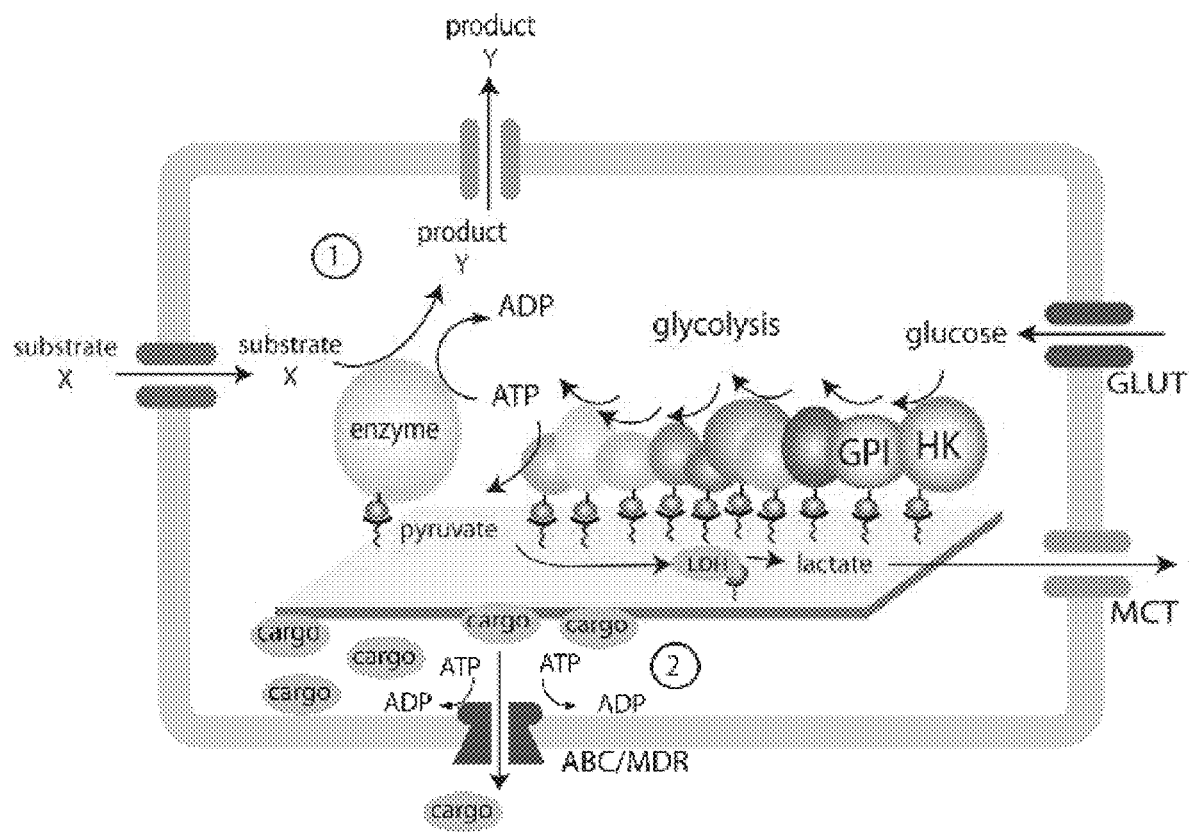
FIG. 1 shows a schematic diagram of the design of a potential medical nanodevice. In this image, the support is encapsulated within a liposome, glucose enters through glucose transporters (GLUT), and a tethered glycolytic pathway processes the glucose into ATP which could either 1) catalyze a needed enzymatic reaction that is co-tethered to the support, or 2) power a membrane "pump" such as an ABC transporter, which would release cargo such as chemotherapy drugs or antibiotics contained within the liposome. "Waste" in the form of pyruvate would be converted to lactate by adding one additional enzyme (LDH), and would then be removed through another transporter (MCT). Adding this capability would allow replenishment of a needed intermediate for glycolysis to continue to function. Priming amounts of ATP, and ADP, inorganic phosphate, and nicotinamide adenine dinucleotide ($NAD^+$) would also be co-encapsulated in the device to support the needed reactions.
Figure 3:
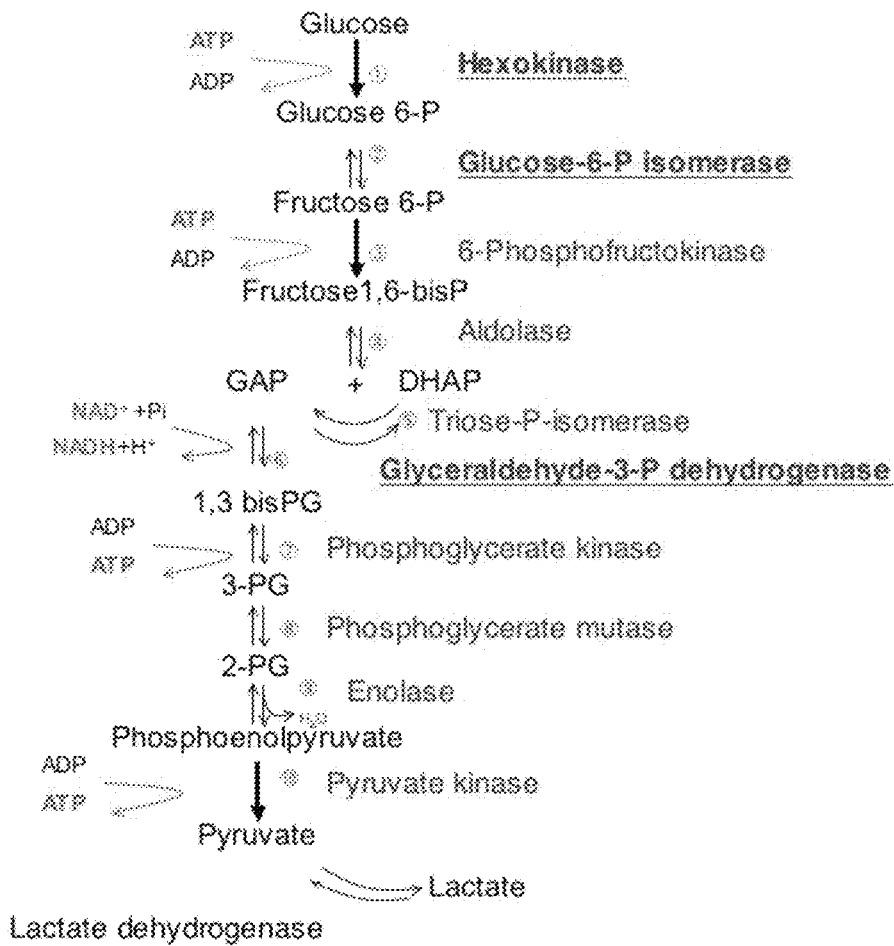
FIG. 3 shows the location of the enzymes within the complete glycolytic pathway where glucose or fructose is metabolized. The conversion of pyruvate to lactate via lactate dehydrogenase is shown as an additional step, because of its potential practical significance as discussed herein.

FIG. 1 provides a schematic drawing of a device in accordance with the present invention with an encapsulated support where glucose enters through glucose transporters ("GLUT"). A tethered glycolytic pathway, comprising a plurality of enzymes, processes the glucose into pyruvate, yielding ATP (2 net molecules of ATP are derived from each molecule of glucose). A schematic representation of this pathway is shown in FIG. 3. In this pathway, glucose is converted to glucose 6-P by hexokinase, and glucose 6-P is transformed with glucose 6-isomerase to fructose 6-P. 6-phosphofructokinase converts fructose 6-P to fructose 1,6-bisP. Aldolase transforms fructose 1,6-bisP to GAP and DHAP. GAP is transformed to 1,3-bisPG with glyceralde-hyde-3-P dehydrogenase. The product of that reaction is converted to 3-PG with phosphoglycerate kinase. 3-PG is converted to 2-PG with phosphoglycerate mutase. Enolase transforms 2-PG to phosphoenolpyruvate. Pyruvate kinase converts phosphoenolpyruvate to pyruvate. In some instances, pyruvate is converted to lactate with lactate dehydrogenase.

Figure 2:
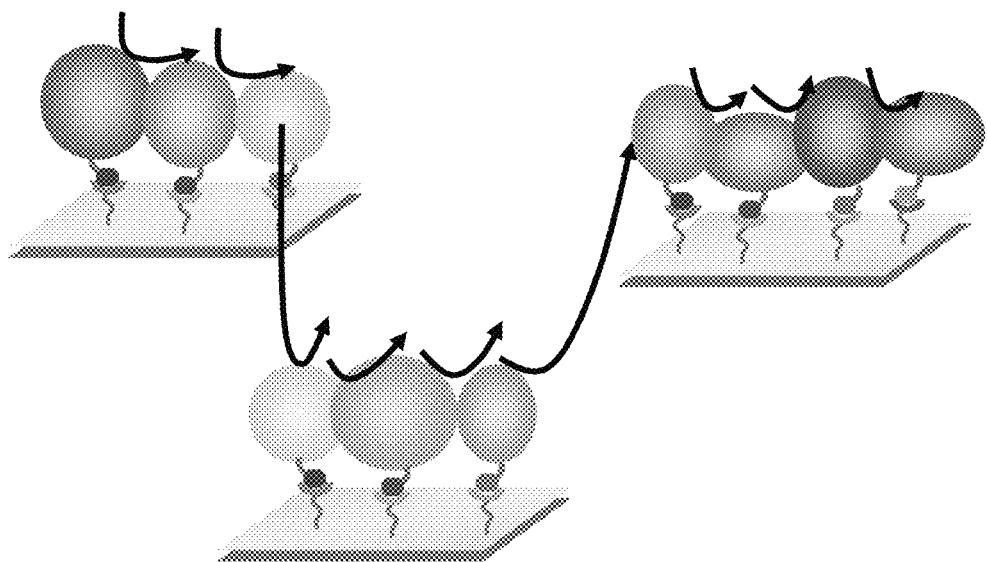
FIG. 2 shows the use of chip sub-assemblies instead of having all 10 (or 11, if LDH is included) enzymes on a single chip.

The enzymes or proteins involved in glycolysis may be linked to one or more support. In that instance, each set of tethered enzymes carries out their sequential step in the production of ATP, then the product of that reaction fuels the next part of the reaction carried out by another enzyme tethered to the same or a different support. The latter embodiment is shown in FIG. 2 which demonstrates that the enzymes of glycolysis may be divided and tethered to separate supports while still carrying out the entire glycolytic pathway. This is advantageous, because each enzyme to be tethered may be coupled to the surface with different attachment chemistries to facilitate their precise patterning. By having fewer enzymes attached to a particular surface, the demand for different attachment chemistries to couple different enzymes will be reduced. This is because different enzymes can be coupled to different surfaces with the same attachment chemistry.

The ATP produced in the device of FIG. 1 could either 1) catalyze a needed enzymatic reaction where the requisite enzyme is co-tethered to the support or 2) power a membrane "pump." In carrying out the former application, substrate x enters the device where it comes into contact with an enzyme coupled to the solid support where that enzyme converts substrate x to product y. Product y is then exported from the device. In powering a membrane pump, ATP drives the ATP binding cassette ("ABC") transporter or the multi-drug transporter ("MDR"), causing the release of cargo (e.g., chemotherapy drugs or antibiotics) contained within the liposome. Waste in the form of pyruvate is converted to lactate by the enzyme lactate dehydrogenase. To remove the lactate, monocarboxylate transporters ("MCT") are positioned in the encapsulating agent. This allows the reactions to proceed without inhibition by end products or a change in pH. A solute carrier family 2 transporter or glucose transporter ("GLUT") can be positioned in the encapsulating agent to convey glucose or fructose to the enzymes coupled to the support. The encapsulating agent may also include an inlet for a substrate and an outlet for a reaction product. The inlets and outlets are, for example, channels, transporters, and/or pores.

In one embodiment of the present invention, hexokinase, glucose 6-phosphate isomerase, 6-phosphofructokinase, aldolase, triose-phosphate-isomerase, glyceraldehyde-3-phosphate-dehydrogenase, phosphoglycerate kinase, phosphoglycerate mutase, enolase, and pyruvate kinase are attached to solid support.

The enzymes can be arranged serially on the support in positions selected to serially carry out the production of ATP from glucose or fructose metabolism. In addition, lactate dehydrogenase may be coupled to the support in a position to carry out the conversion of pyruvate to lactate. In this way, $NAD^+$ may be replenished to perform subsequent glycolysis reactions.

Although many different potential attachment chemistries exist, one coupling mechanism replaces the targeting or scaffolding domains of glycolytic enzymes with an enzyme that binds a linking agent coupled to the nano-particle support. One coupling mechanism replaces the targeting or scaffolding domains of glycolytic enzymes with a polyhistidine-tag ("His-tag"). Yet another coupling mechanism replaces the targeting domains of glycolytic enzymes with a glutathione S-transferase ("GST fusion tag") fusion tag. The His-tag and GST fusion tag allow the recombinant proteins to bind to a linking agent that is affixed to a solid surface.

Suitable linking agents include, but are not limited to, nickel nitrilotriacetate or glutathione.

Optionally, the supports are first coated. Suitable coatings include, but are not limited to, polyethylene glycol or gold.

Suitable encapsulating agents for the device of the present invention include, but are not limited to, liposomes, silastic implants, and Teflon implants. The use of encapsulating agents is well known in the field.

Another embodiment of the device may also include an enzyme positioned on or coupled to the support to phosphorylate a substrate.

In yet another embodiment of the invention, the components associated with the system carry out a biological or biochemical reaction.

The present invention also relates to a method for carrying out a reaction involving the conversion of ATP to ADP. This method involves providing a system for producing ATP from glucose or fructose metabolism. The system includes a support and one or more enzymes coupled to the support that are capable of collectively producing ATP from glucose or fructose metabolism. The system is contacted with glucose or fructose under conditions effective to produce ATP from glucose or fructose metabolism. The ATP is converted to ADP and the reaction is carried out.

In carrying out this method, the system can be substantially the same as that described above.

Figure 4:
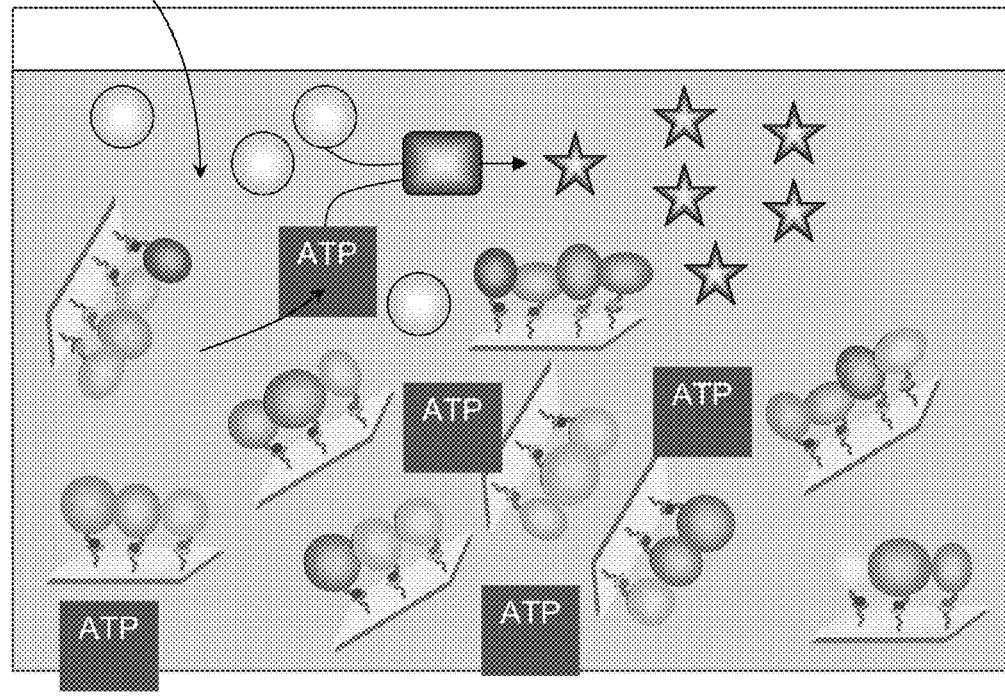
FIG. 4 shows ATP produced by means of the present invention used for the production of engineered molecular products (e.g. specific forms of proteins, nanoparticles, or more complex "molecular machines"—groups of proteins that can function together). This could be either large scale or small scale.

The method of the present invention can also include a step of priming the system with an agent such as ATP, NAD+, or Pi. This is generally shown by FIG. 4 where the repeated additions of glucose and substrates is additionally depicted. By priming the device with intermediates, starting materials, and/or cofactors for the system to use during glycolysis, ATP is produced continuously and able to drive the reaction forward indefinitely (up to the lifespan of the proteins on the device). The amount of glycolytic ATP production also could control the rate of reaction (as opposed to ATP in the encapsulating agent which would allow the enzyme run at its full kinetic speed). Thus, a carefully designed device pumps out a given amount of its product at a defined rate through a component in the encapsulating agent's membrane so long as blood glucose is kept within a specific range. The production of the ATP may also be linked to the uptake of glucose so that the device would not perform its function until glucose enters the device. This provides an additional level of control if the device is encapsulated in a second outer layer of protective membrane or matrix, that would degrade over a given period of time and then allow glucose to activate the device. In this way, one could easily create a variety of sub-sets of devices engineered for a delayed release of their contents, and the mixture of sub-types would determine the rate and duration of release.

Figure 6:
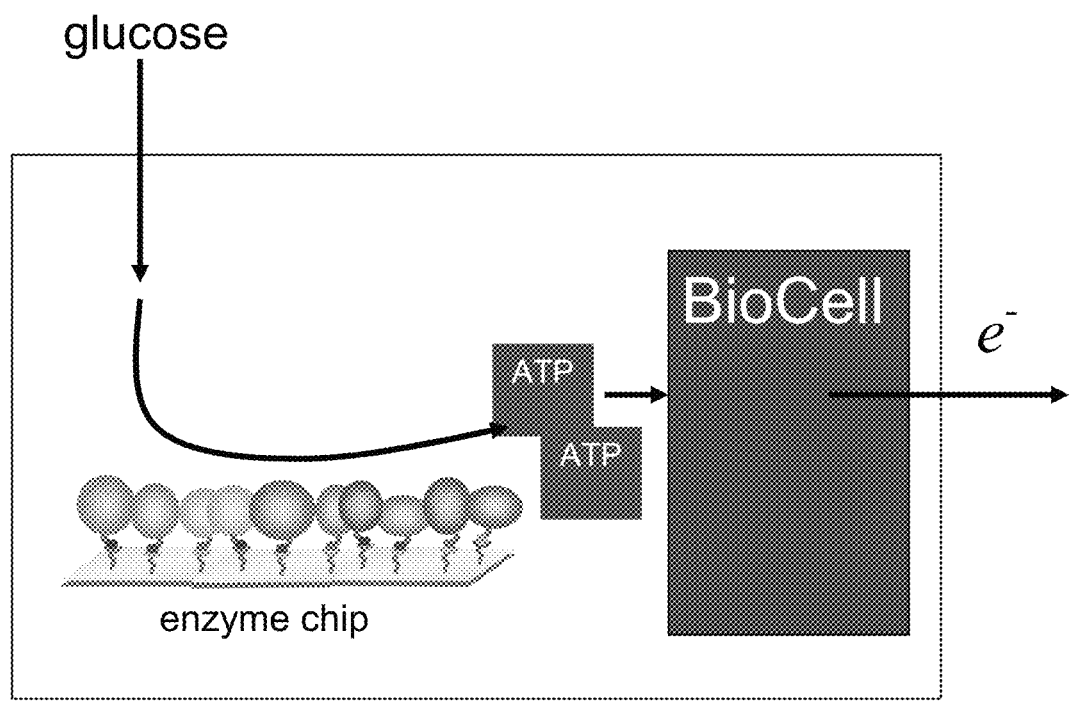
FIG. 6 shows the technology of the present invention that could potentially be linked with the "Bio-Cell" or other technologies that use ATP to produce electricity, whether a single device or multiple sub-assemblies. Applications might include generating electricity in a body to power a pump, pacemaker, defibrillator, or other device requiring electricity. Alternatively, the power can be used to recharge a battery for such devices.

In yet another embodiment of the present invention, the ATP produced by the nano-particle system is used to fuel a bio-cell (See FIG. 6) or other technology to produce electricity.

In one embodiment, ATP is used to carry out a reaction, such as the conversion of ATP to ADP, whereby hydrogen is produced. This hydrogen then moves across a membrane to produce electricity. The hydrogen may also be used with the components of an encapsulating agent to facilitate intercellular transport.

A further embodiment of the present invention also relates to a method for producing ATP. This involves providing a system for producing ATP from glucose or fructose metabolism. The device includes a support and one or more enzymes coupled to the support that are capable of collectively producing ATP from glucose or fructose metabolism. The system is contacted with glucose or fructose under conditions effective to produce ATP from glucose or fructose metabolism.

Figure 5:
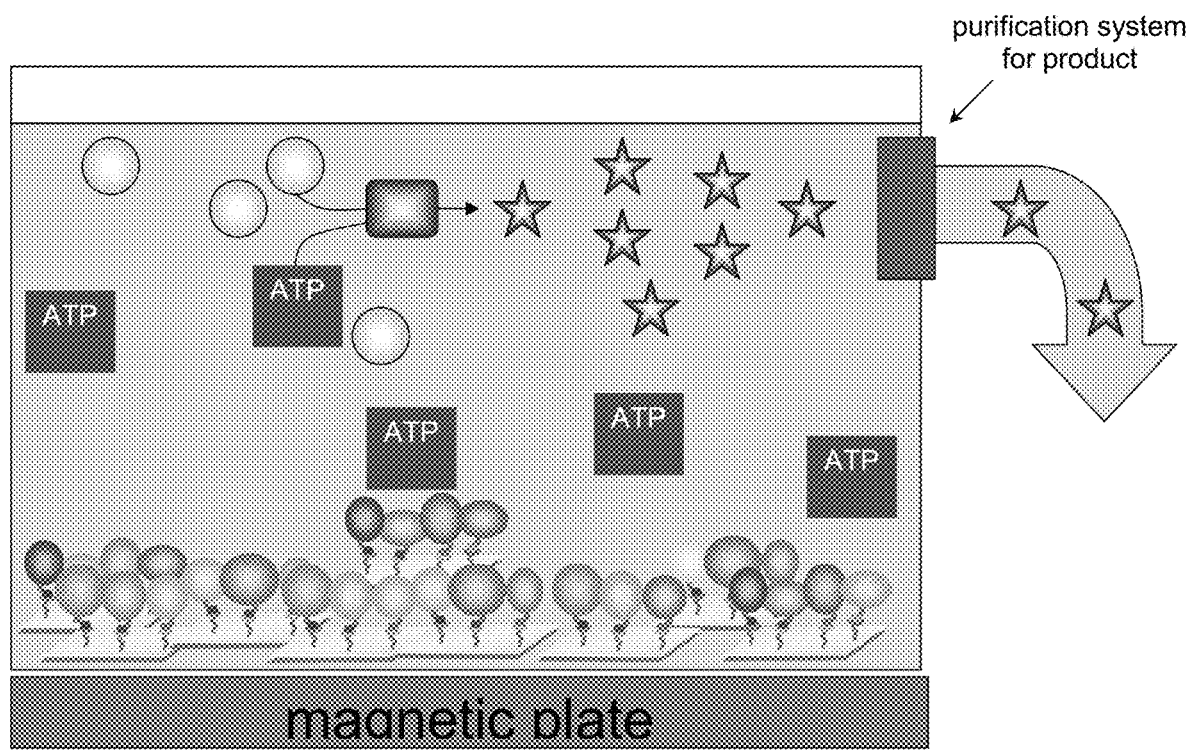
FIG. 5 shows one way of removing the ATP-generating nanodevices from the application shown in the previous slide. If the devices were magnetic, they could potentially be separated with the application of a magnet.

As shown generally in FIG. 5, in yet another embodiment of the present invention, the ATP generating system of the present invention may power other secondary nano-particle supports or subassemblies that are coupled to one or more enzymes or proteins that may or may not function together. These secondary subassemblies can include a specific form of enzyme or protein, a nano-particle, and/or a more complex molecular machine in which the enzymes or proteins coupled to the support or supports act in concert, as shown in FIG. 5.

For example, groups of enzymes may be coupled together on a separate support from the system of the present invention, which requires ATP to function or carry out a reaction. This secondary structure may also carry a single enzyme or protein that is functionalized upon contact with ATP or a substrate. The secondary structures may also act together by releasing products of enzymatic reactions and thus triggering a reaction or event on another secondary subassembly. Moreover, the ATP produced by the device of the present invention can fuel a more complicated molecular factory, whereby a substrate is converted to an engineered molecular product through a series or cascade of reactions within the molecular factory.

In this embodiment, unwanted subassemblies or supports can be removed by the application of a magnet to the device. In one embodiment, when a magnet is applied to this device, it may be possible to purify the product of other secondary assemblies or structures as shown in FIG. 5. More specifically, the magnetized nanoparticles can be functionalized so that the desired substrate or product of reactions can be separated from the magnetized structures. This is well known in the field (Barry et al., "Applications of Magnetic Nanoparticles in Biomedicine," *J. Phys. D: Appl. Phys.* 36:R198-R206 (2003), which is hereby incorporated by reference in its entirety).

EXAMPLES

The following examples are provided to illustrate embodiments of the present invention but are by no means intended to limit its scope.

Example 1—Generation of Recombinant Hexokinase and Glucose-6-Phosphate Isomerase All reagents were purchased from Sigma (St. Louis, Mo.), unless otherwise indicated. Full-length HK1-sc and somatic GPI were cloned from mouse testis by RT-PCR using the following primers, 5'-ATGGGACAGAACTGCCAGCGAGGAC-3' (SEQ ID NO:1)(forward, HK1-sc), 5'-TTAGGCGTTCGTAGGGTCTCCTCTGAGCC-3' (SEQ ID NO:2) (reverse, HK1-sc), 5'-ATGGCTGCGCT-CACCCGGAACC-3' (SEQ ID NO:3) (forward, GPI), and 5'-TTATTCTAGTTTGGTGTCCCGCTGTTGC-3' (SEQ ID NO:4) (reverse, GPI). The germ cell-specific targeting domain of HK1-se was removed by nested PCR using another forward primer, 5'-GAAAAGATTGA-TAAGTATCTGTATGCCATGCGGC-3' (SEQ ID NO:5). HK and GPI cDNA were cloned into the expression vector pcDNA4/HisMax TOPO TA (Invitrogen), which added a 6 histidine repeat on the amino terminus, followed by an enterokinase cleavage site and then the glycolytic enzyme's sequence. Constructs were validated by sequencing and then were transfected into HEK293-F-FreeStyle cells (Invitrogen, Carlsbad, Calif.), using the 293Fectin™ transfection reagent (Invitrogen). The protein was purified from cell lysates 48 h later using a Ni-NTA purification system (Invitrogen). The purified proteins were dialyzed with 1 L of 50 mM MOPS, 3 times, and then concentrated using Amicon filtration centritubes (Millipore, Billerica, Mass.). Protein concentrations were determined with the Micro-BCA assay (Pierce, Rockford, Ill.), and purity of the samples was analyzed by SDS-PAGE and immunoblotting. The primary antibodies used were as follows: mouse anti-His tag (1:5000 dilution, Invitrogen), mouse anti-type1 hexokinase (1:1000 dilution, Chemicon, Temecula, Calif.), and rabbit anti-GPI (1:500 dilution, Santa Cruz Biotechnology, Santa Cruz, Calif.). The secondary antibodies used were ECL anti-mouse IgG and ECL anti-rabbit IgG, both conjugated with horseradish peroxidase (Amersham, GE Healthcare, Piscataway, N.J.).

Example 2—Generation of Recombinant HK1 and GPI

The cDNA of a germ cell-specific isoform of HK1 (HK1-sc), and GPI were obtained by RT-PCR from mouse testis RNA, and the germ cell-specific targeting domain of HK (Travis A J, et. al, *J. Biol. Chem.* 274, 34467-34475 (1990), which is hereby incorporated by reference in its entirety) (describing murine and human GCS domains as including the amino acid sequences of MGQNCQRGQAVDVEP-KIRPPLTEE (SEQ ID NO: 6, murine) and MGQICQRE-SATAAEKPKLHLLAES (SEQ ID NO: 7, human)) was removed by nested PCR. The constructs were inserted into a vector that places a hexahistidine tag at the amino terminus, thus replacing the HK1-sc germ cell-specific targeting domain. His-HK and His-GPI were expressed in a mammalian expression system and then purified using a Ni-NTA system. The products were separated using SDS-PAGE and their purity and identity were respectively checked through the use of Coomassie staining and immunoblotting with antibodies against the proteins and against the His-tag. Both recombinant enzymes were found to be highly pure (80-90%, with only slight variations between sample preparations), immunoreactive with the appropriate antibodies, and to migrate at the expected molecular weights (FIG. 7).

Example 3—Quantification of His-HK and His-GPI Enzyme Activities

The activity of recombinant proteins individually in solution was examined by means of a coupled reaction pathway, ultimately measuring the reduction of NADP$^+$ by a change in absorbance at 340 nm. For both reactions, exogenous glucose-6-phosphate dehydrogenase (G6PDH) was added, as described above. It was confirmed that the changes in absorbance specifically measured the target enzyme activities by running control reactions in the absence of exogenous G6PDH or substrate, and comparing the values from the experimental proteins versus commercially available purified HK1 and GPI.

His-HK demonstrated activity without the germ cell targeting region, with a $V_{max}$ equal to 11.67 U/mg, and a $K_m$ equal to 0.274 mM (glucose) (Table 1).

TABLE 1

| | $V_{max}$ | $K_m$ |
|---|---|---|
| His-HK | 11.67 ± 5.82 | 0.274 ± 0.12 |
| His-GPI | 48.89 ± 8.89 | 0.226 ± 0.086 |

This result was very similar to the values obtained for a commercial HK enzyme in solution ($V_{max}$=12.33 U/mg. $K_m$=0.245 mM glucose). These results demonstrated that the recombinant HK remained functional with the germ cell-specific domain replaced by the hexahistidine-tag. The activity of the His-HK, when adsorbed to a gold wafer with a Ni-NTA surface (FIG. 8A), was next tested. The recombinant showed activity on the surface, with negative controls being the recombinant on the chip in the absence of the exogenous reaction components, and also a blank Ni-NTA chip in the presence of the reaction components. To identify the value of co-opting the germ cell-specific targeting domain, several attempts to generate a recombinant HK lacking either the native targeting domain or the His-tag (by means of the enterokinase site provided by the vector) were made. These proteins were highly labile, and their degradation prevented interpretable comparative data from being obtained.

A similar approach was used with His-GPI, which had a $V_{max}$ equal to 48.89 U/mg, and a $K_m$ equal to 0.226 mM (fructose 6-phosphate) when tested in solution (Table 1). Unlike the HK, it was possible to utilize enterokinase (Novagen, EMD/Merck, Madison, Wis.) to remove the His-tag. Enterokinase resin and Ni-NTA agarose were used to remove the residual enterokinase and the protein from the cleaved His-tag. It was then confirmed that there was no His-GPI remaining by means of SDS-PAGE and immunoblotting using an antibody against the His tag. After the cleavage, the kinetic activity of the GPI protein was checked with similar results. The GPI construct without the His-tag had a Vmax equal to 51.28 U/mg, and a Km equal to 0.308 mM (fructose 6-phosphate). As with the HK, these values were very similar to those obtained for the commercial enzyme ($V_{max}$: 54.054 U/mg, $K_m$: 0.476 mM fructose 6-phosphate). Both experimental and control GPI recombinant proteins were stable for more than 2 months when stored at 4° C.

The activity of the His-GPI (FIG. 8B) when tethered to the Ni-NTA gold chips was next tested. The recombinant showed activity when adsorbed to the surface, showing that the recombinant was functional even when tethered. The adsorption and specific activities on the chips were significantly different between His-GPI and the control GPI, which had the His-tag removed with enterokinase (FIG. 9). Thus, the amino-terminal attachment provided not only a higher amount bound to the chip, but also significantly higher activity for each unit of protein bound.

Example 4—Preparation of Ni-NTA Surface and Protein Immobilization

To determine the amount of protein bound to a chip, the concentration of the solution was quantified before and after adsorption. Ellipsometry was utilized to corroborate this finding by determining the relative thickness of the protein layer adsorbed to the surface.

Example 5—Spectrophotometric Analysis of His-HK and His-GPI Activity

HK and GPI activity were measured by means of coupled enzyme reaction pathways that led to the reduction of NADP$^+$ to NADPH. The rate of this reduction was measured as a change in absorbance at 340 nm using a spectrophotometer (SAFIRE microplate reader, Tecan, Medford, Mass.). The coupled reactions for HK were as follows: glucose+ATP→glucose-6-phosphate+ADP and glucose-6-phosphate+NADP$^+$→NADPH+6-phospho-glucono-δ-lactone, with the first reaction catalyzed by His-HK, and the second catalyzed by exogenous glucose 6-phosphate dehydrogenase (G6PDH). The coupled reactions for GPI were as follows: fructose-6-phosphate-glucose-6-phosphate and glucose-6-phosphate+NADP$^+$→NADPH+6-phospho-glucono-δ-lactone, with the first reaction catalyzed by His-GPI, and the second catalyzed by exogenous G6PDH. Fresh stocks of NADP$^+$ and ATP were prepared immediately prior to each trial. The base reaction mixture contained 1 mM NADP$^+$, 10 mM $MgCl_2$, and 3 U/ml G6PDH in 50 mM MOPS buffer (pH 7.4). To quantify HK activity, 1 mM ATP and 5 mM glucose were added. To quantify GPI activity, 5 mM fructose 6-phosphate was added. Measurements of activity were determined from slopes taken from within the linear range. The $K_m$ and $V_{max}$ for each enzyme were calculated by quantifying the enzymatic activities at various concentrations of their respective substrates and fitting the data to hyperbolic functions. One unit of enzyme activity was defined as the amount of enzyme that catalyzed the formation of 1 μmol of NADPH per min.

Example 6—Tethering of Enzymes to Inorganic Supports and Quantification of Activity while Bound The proteins were adsorbed by placing 60 μl of 50 mM MOPS (pH 7.4) containing known amounts of protein, at room temperature in the dark on a single gold Ni-NTA surface (1×1 cm square). After 15 min, 50 μl of the solution was removed by pipetting, and 90 μl of the MOPS buffer was gently added to the surface. This volume was then collected and combined with the 50 μl that had been removed for the purpose of quantifying the amount of protein that did not bind. Two more washes with 90 µl volumes of the MOPS buffer were performed, and these were also collected individually for quantification of protein that was removed. The concentrations of protein in these three volumes were determined using the Micro-BCA protein assay and the amount of the protein left on the chip was calculated by subtraction. It should be noted that the amounts of protein removed by the second and third washes were consistently below the levels of detection. To ensure that all unbound or loosely bound protein was removed, the surface was then gently washed with 5 ml of MOPS buffer 3 times. Thus, it should be noted that for the purposes of quantification of specific activity, the amounts of protein bound were equal to or less than the amounts quantified, giving a conservative error.

The enzyme reactions themselves were carried out in a well with the chip in a 1 ml volume of reaction mixture. The change in absorbance at 340 nm at various time points was measured by removing 300 µl of reaction mixture and transferring that to another well within the plate. Readings were obtained using a spectrophotometer as above. One unit of enzyme activity was defined as the amount of enzyme that catalyzed the formation of 1 µmol of NADPH per min. All assays were performed at least 3 times, each with at least triplicate sets of chips. Negative controls included the Ni-NTA surface alone and the surface with adsorbed protein, but missing the exogenous substrate. Comparative measurements were obtained using chips adsorbed with the His-tagged recombinants versus recombinants made without the His tag, or versus recombinants that had the His tag removed by enterokinase cleavage.

To determine whether His-HK and His-GPI could act in series, the proteins were immobilized by placing 60 µl of mixed protein solution (0.5 nM His-HK, 0.5 nM His-GPI in 50 mM MOPS buffer, pH 7.4) at room temperature in the dark on a single gold Ni-NTA surface (1×1 cm square). After 1 h, the surface was gently washed with 5 ml of MOPS buffer 3 times. The assay of the sequential reaction of HK-GPI was performed at room temperature by measuring the oxidation of NADH at 340 nm as a result of exogenous glycerol 3-phosphate dehydrogenase. The reaction was carried out in a similar fashion as those for HK and GPI individually, with the reaction mixture containing 50 mM MOPS, 5 mM glucose, 1 mM ATP, 0.5 mM NADH, 2 mM $MgCl_2$, 0.5 U/ml phosphofructokinase, 0.5 U/ml aldolase, 7 U/ml triose phosphate isomerase, and 2 U/ml glycerol 3-phosphate dehydrogenase at pH 7.4. Fresh stocks of NADH and ATP were prepared immediately prior to each trial. One unit of coupled reaction activity was defined as the amount of enzyme that catalyzed the formation of 1 µmol of $NAD^+$ per min. All assays were performed at least 3 times, each with at least triplicate sets of chips. Negative controls included the Ni-NTA surface alone, the surface with both adsorbed proteins but missing the exogenous substrate, or His-HK and the pathway reagents, or His-GPI and the pathway reagents. Comparative measurements were obtained using chips adsorbed with the His-tagged recombinants versus recombinants that had the His tag removed by enterokinase cleavage.

Example 7—His-HK and His-GPI Reactions in Series on a Single Device

Figure 10:
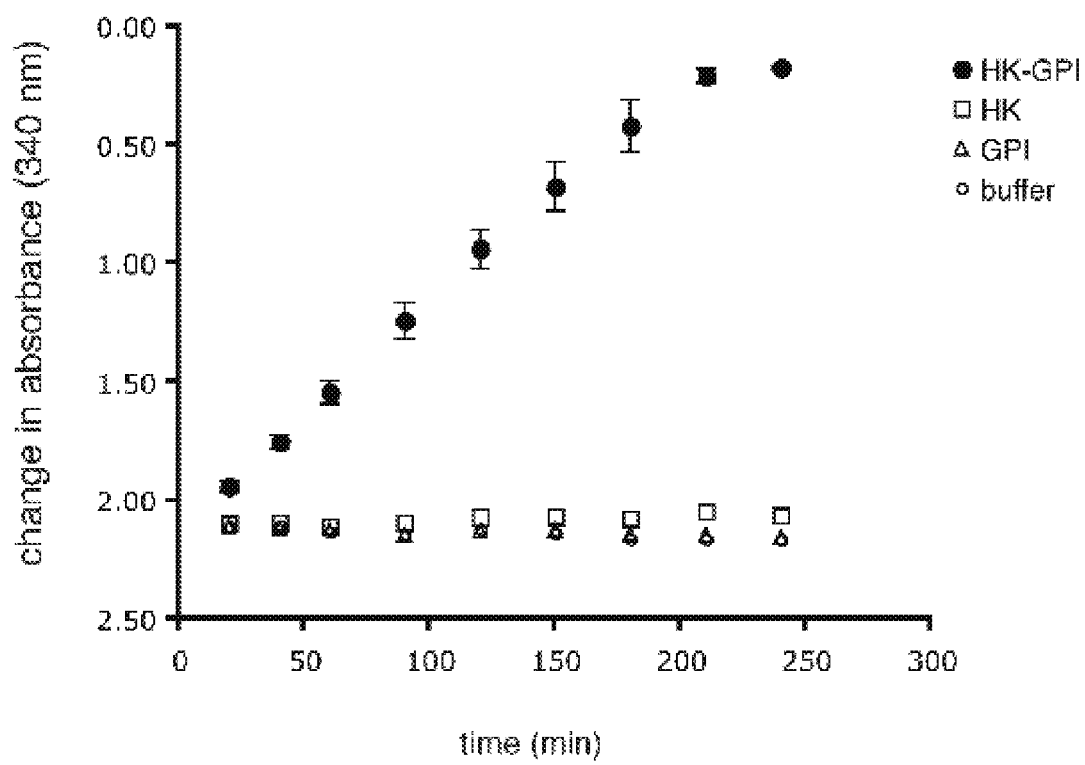
FIG. 10 shows His-HK and His-GPI were tethered together, allowing glucose to be catalyzed sequentially to glucose-6-phosphate and then to fructose-6-phosphate. Completion of the reaction was detected by the coupled reaction pathway as described. "HK-GPI" denotes supports incubated with 0.5 nM His-HK and 0.5 nM His-GPI. Readings for supports incubated with His-HK alone (HK) or His-GPI alone (GPI) were taken with protein solutions at 1 nM concentration. A blank was performed with the Ni-NTA surface incubated in MOPS buffer (buffer). This figure shows a representative result from one set of protein preparations, with triplicate samples (Bars denote standard deviations). Because binding might be predicted to differ slightly for each protein for each set of preparations, it would not be valid to pool the data for the experiments; however, the experiment was performed with three separate sets of preparations with very similar results each time.

The recombinant His-HK and His-GPI were next mixed in several different molar ratios and attached them to a single Ni-NTA coated surface. These two enzymes are the first two steps of glycolysis. After thorough rinsing, sequential enzymatic activities of the tethered recombinant proteins was tested, and it was found that the two enzymes did in fact act in series, metabolizing glucose into fructose 6-phosphate (FIG. 10). Controls included adsorbing His-HK alone with the complete reagents for the coupled reaction pathway, and His-GPI alone with the complete reagents for the coupled reaction pathway, and with the buffer alone. All controls gave equivalent baseline readings (FIG. 10), confirming that the change in absorbance resulted from the activity of the tethered enzymes. Only the two enzymes together showed activity under the coupled reaction pathway that was employed. This demonstrated that the reaction buffer and its individual components were not contaminated with either of the enzymes, nor other chemicals that would cause a change in absorbance in the presence of either enzyme.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A method for producing adenosine triphosphate, said method comprising:
   providing a system for production of adenosine triphosphate, said system comprising:
      a support comprising a linking agent that binds a targeting domain and
      one or more enzymes positioned in the system to collectively produce adenosine triphosphate from glucose or fructose metabolism, wherein a germ cell-specific targeting/scaffolding domain of at least one of said one or more enzymes has been replaced with a targeting domain that specifically binds to the linking agent of the support to couple the at least one of said or more enzymes to the support; and
   contacting the system with glucose or fructose under conditions effective to produce adenosine triphosphate.

2. The method of claim 1 further comprising:
   conveying glucose to the system.

3. The method of claim 1 further comprising:
conveying pyruvate and/or lactate from the system.

4. The method of claim 1, wherein said one or more enzymes comprise hexokinase, glucose 6-phosphate isomerase, 6-phosphofructokinase, aldolase, triose-phosphate-isomerase, glyceraldehyde-3-phosphate-dehydrogenase, phosphoglycerate kinase, phosphoglycerate mutase, enolase, and pyruvate kinase.

5. The method of claim 1 further comprising:
converting pyruvate to lactate with a lactate dehydrogenase coupled to the support.

6. The method of claim 1, wherein the targeting/scaffolding domain of the at least one enzyme of said one or more enzymes is replaced with a histidine tag and the support is provided with a linking agent which binds to the histidine tag or the targeting/scaffolding domain of the at least one enzyme of said one or more enzymes is replaced with a GST fusion tag and the support is provided with a linking agent which binds to the GST fusion tag.

7. The method of claim 6, wherein the linking agent is nickel nitrilotriacetate or glutathione.

8. The method of claim 1, wherein the support is coated with polyethylene glycol or gold.

9. The method of claim 1, wherein the system is initially primed with $NAD^+$, ADP, and/or ATP.

10. The method of claim 1, wherein the at least one of said one or more enzymes is pyruvate kinase.

11. The method of claim 1, wherein the at least one of said one or more enzymes is hexokinase.

12. The method of claim 1, wherein the at least one of said one or more enzymes is hexokinase and the targeting/scaffolding domain comprises the amino acid sequence of GQNCQRGQAVDVEPKIRPPLTEE (SEQ ID NO: 6) or MGQICQRESATAAEKPKLHLLAES (SEQ ID NO: 7).

13. The method of claim 1, wherein the at least one of said one or more enzymes is glyceraldehyde 3-phosphate dehydrogenase.

14. The method of claim 1, wherein the at least one of said one or more enzymes is aldolase.

15. The method of claim 1, wherein said support and said one or more enzymes are encapsulated in an encapsulating agent.

16. The method of claim 15, wherein the encapsulating agent is selected from the group consisting of a liposome and silastic implant.

17. The method of claim 15, wherein the encapsulating agent comprises a silastic material.

18. The method of claim 15, wherein said support and said one or more enzymes are encapsulated in a single chamber defined by the encapsulating agent.

19. The method of claim 1, wherein the system is contained within a device.

20. The method of claim 19 further comprising:
releasing an agent from the device as a result of the adenosine triphosphate interacting with a member of an adenosine triphosphate binding cassette family of transporters.

21. The method of claim 1 further comprising:
conveying fructose to the system.

* * * * *

SEQUENCE LISTING

<160> NUMBER OF SEQ ID NOS: 7

<210> SEQ ID NO 1
<211> LENGTH: 25
<212> TYPE: DNA
<213> ORGANISM: Artificial
<220> FEATURE:
<223> OTHER INFORMATION: Forward primer for HK1-sc

<400> SEQUENCE: 1
atgggacaga actgccagcg aggac                                          25

<210> SEQ ID NO 2
<211> LENGTH: 29
<212> TYPE: DNA
<213> ORGANISM: Artificial
<220> FEATURE:
<223> OTHER INFORMATION: Reverse primer for HK1-sc

<400> SEQUENCE: 2

```
ttaggcgttc gtagggtctc ctctgagcc                                          29
```

<210> SEQ ID NO 3
<211> LENGTH: 22
<212> TYPE: DNA
<213> ORGANISM: Artificial
<220> FEATURE:
<223> OTHER INFORMATION: Forward primer for GPI

<400> SEQUENCE: 3

```
atggctgcgc tcacccggaa cc                                                 22
```

<210> SEQ ID NO 4
<211> LENGTH: 28
<212> TYPE: DNA
<213> ORGANISM: Artificial
<220> FEATURE:
<223> OTHER INFORMATION: Reverse primer for GPI

<400> SEQUENCE: 4

```
ttattctagt ttggtgtccc gctgttgc                                           28
```

<210> SEQ ID NO 5
<211> LENGTH: 34
<212> TYPE: DNA
<213> ORGANISM: Artificial
<220> FEATURE:
<223> OTHER INFORMATION: Forward primer for removal of HK1-sc

<400> SEQUENCE: 5

```
gaaaagattg ataagtatct gtatgccatg cggc                                    34
```

<210> SEQ ID NO 6
<211> LENGTH: 24
<212> TYPE: PRT
<213> ORGANISM: Mus musculus

<400> SEQUENCE: 6

```
Met Gly Gln Asn Cys Gln Arg Gly Gln Ala Val Asp Val Glu Pro Lys
1               5                   10                  15

Ile Arg Pro Pro Leu Thr Glu Glu
            20
```

<210> SEQ ID NO 7
<211> LENGTH: 24
<212> TYPE: PRT
<213> ORGANISM: Homo sapiens

<400> SEQUENCE: 7

```
Met Gly Gln Ile Cys Gln Arg Glu Ser Ala Thr Ala Ala Glu Lys Pro
1               5                   10                  15

Lys Leu His Leu Leu Ala Glu Ser
            20
```